US00PP35143P2

(12) United States Plant Patent
Carruth

(10) Patent No.: US PP35,143 P2
(45) Date of Patent: May 2, 2023

(54) HYBRID TEA ROSE PLANT NAMED 'WEKVODOMER'

(50) Latin Name: *Rosa hybrida*
Varietal Denomination: WEKvodomer

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 17/803,754

(22) Filed: Nov. 9, 2022

(51) Int. Cl.
*A01H 5/02* (2018.01)
*A01H 6/74* (2018.01)

(52) U.S. Cl.
USPC ..... Plt./136

(58) Field of Classification Search
USPC ..... Plt./101, 130, 136
See application file for complete search history.

(56) References Cited

U.S. PATENT DOCUMENTS

PP5,165 P 12/1983 Kriloff
PP6,121 P 3/1988 Christensen

*Primary Examiner* — Karen M Redden
(74) *Attorney, Agent, or Firm* — McKee, Voorhees & Sease, PLC

(57) ABSTRACT

A new variety of Hybrid Tea rose suitable for garden decoration, having flowers of salmon coloration.

1 Drawing Sheet

Classification: The present disclosure relates to a new *Rosa hybrida* plant.

Variety denomination: The new plant has the varietal denomination 'WEKvodomer'.

BACKGROUND OF THE INVENTION

This invention relates to a new and distinct variety of Hybrid Tea Rose. It has as its seed parent the variety known as 'AROmiclea' (U.S. Plant Pat. No. 6,121) and as its pollen parent the variety known as 'WEKmeredoc' (not patented). It was hybridized by Applicant.

SUMMARY OF THE INVENTION

Among the features which distinguish the new variety from other presently available and commercial rose cultivars known to the Applicant are the following combinations of characteristics: its strong fruity and spicy fragrance, its elegant high centered flower of salmon coloration, its excellent color stability throughout the life of the flower, and its abundant bloom. The plant has an upright growing habit, suitable for outdoor garden decoration.

Asexual reproduction of the new variety by budding as performed in Kern County, Calif., shows that the foregoing and other distinguishing characteristics come true to form and are established and transmitted through succeeding asexual propagations. 'WEKvodomer' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'AROmiclea' by the following combination of characteristics: 'WEKvodomer' bears very double flowers (about 60 to 138 petals) of salmon coloration, 'AROmiclea' bears double flowers of peachy-orange coloration blushed scarlet on finish with significantly lesser petalage (about 30 to 35 petals). The new variety has an upright tall growing habit (about 155 to about 195 cm. in height), whereas the seed parent has an upright moderately spreading significantly shorter growing habit (about 150 cm. in height).

The new variety may be distinguished from its pollen parent, 'WEKmeredoc' by the following combination of characteristics: 'WEKvodomer' bears very double flowers (about 60 to 138 petals) of salmon coloration, 'WEKmeredoc' bears double flowers of light pink coloration with darker undertones and with significantly lesser petalage (about 26 to 40 petals). The new variety has an upright tall growing habit (about 155 to about 195 cm. in height), whereas the pollen parent has an upright slightly spreading significantly shorter growing habit (about 90 cm. in height).

COMPARISON WITH THE CLOSEST COMMERCIALLY AVAILABLE CULTIVAR

The new variety may be distinguished from its closest commercially available cultivar, 'KRIcarlo' (U.S. Plant Pat. No. 5,165) by the following combination of characteristics: whereas 'WEKvodomer' bears very double flowers (about 60 to 138 petals) of salmon coloration, 'KRIcarlo' bears double flowers of orange-pink coloration with significantly lesser petalage (about 25 to 35 petals). The new variety has a strong fruity and spicy fragrance, whereas the closest commercially available cultivar has a slight tea fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character.

The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

FLOWER

The new variety usually bears its flowers singly, on strong medium to long stems (about 28 to about 60 cm.). Outdoors, the plant blooms abundantly and nearly continuously during the growing season. The flowers have a strong fruity and spicy fragrance.

BUD

The peduncle is about 2.6 to about 9.4 cm. in length, of average to heavy caliper (about 0.3 to about 0.6 cm. in diameter), and usually erect to somewhat stiff. It is somewhat rough, with few stipitate glands. Peduncle color is between 146C and 152B often heavily suffused, especially on the side exposed to the sun, with between 187B and 187A.

Before the calyx breaks, the bud is about 1.5 to about 1.9 cm. in diameter at the widest point, about 1.8 to about 2.2 cm. in length, and pointed to somewhat ovoid in shape. The surface of the bud bears between 9 to 16 foliaceous appendages, often with stout entire foliaceous parts extending beyond the tip of the bud about ¾ or more of its length. Bud color is between 137C and 146B often moderately suffused, especially on the side exposed to the sun, with between 187B and 187A.

The sepals are 5 per flower, about 2.1 to about 4.9 cm. in length and about 0.8 to about 1.2 cm. in width at the widest point. The outer surface color of the sepal is between 137C and 146B often moderately suffused, especially on the side exposed to the sun, with between 187B and 187A. The outer surface of the sepal is smooth and bears between 0 to 7 foliaceous appendages with some hairs. The inner surface color of the sepal is between 137C and 137B. After the sepals open, the inner surface color is often heavily suffused, especially on the area exposed to the sun, with between 187B and 187A. The inner surface of the sepal is covered with fine wooly tomentum; sepal margins are entire and lined with few stipitate glands and some hairs. The sepals are moderately permanent, and usually straight in shape with acute apices.

The receptacle of the flower is of somewhat short to medium length (about 0.3 to about 0.7 cm.) and moderately thin to average in caliper (about 0.7 to about 1.4 cm. in diameter). The receptacle is cup-shaped in form. Its surface is smooth with moderately thick fleshy walls. The receptacle color is between 144A and 146C.

As the petals open (after the calyx breaks), the bud is about 1.9 to about 3.4 cm. in diameter at the widest point, about 2.1 to about 4.0 cm. in length, and moderately ovoid to somewhat pointed in form. The color of the under surfaces of the newly opened petals is between 35B and 50C often heavily suffused on the outermost petals with between 187B and 187A. At the point where the petal attaches, there is a somewhat large zone of near 145C. The color of the upper surfaces of the newly opened petals is between 40C and 48C. At the point where the petal attaches, there is a somewhat large zone of near 145C.

BLOOM

When fully open, the bloom ranges from about 9.6 to about 13.2 cm. in diameter. Petalage is very double with about 60 to 138 petals and about 5 to 35 petaloids irregularly arranged. When partially open, the bloom form is high centered to moderately cupped, and the petals are tightly spiraled to cupped with petal edges somewhat reflexed outward. When fully open, the bloom form is more cupped, and the petals are loosely cupped with petal edges moderately reflexed outward. Often many of the intermediate and inner petals are folded along the midrib.

PETALS

The substance of the petals is moderately heavy and of somewhat thin to medium thickness, with upper surfaces slightly satiny and under surfaces slightly shiny. The petals are about 2.4 to about 5.6 cm. in length and about 1.9 to about 6.2 cm. in width at the widest point. Petal margins are entire.

The outer petals are nearly round to somewhat obovate in shape with rounded apices sometimes slightly notched with one notch.

The inner petals are broadly obovate in shape with rounded apices and sometimes slightly notched with one notch.

Petaloids are about 1.5 to about 3.7 cm. in length and about 0.4 to about 2.5 cm. in width at the widest point. Petaloids are irregularly shaped moderately oblanceolate to somewhat subulate with rounded to sometimes lacerated apices.

NEWLY OPENED FLOWER

The under-surface color of the outer petals is between 39D and 36A often moderately suffused with between 60A and 60B. At the point where the petal attaches, there is a moderately small zone of between 154D and 1D. The upper surface color of the outer petals is between 38C and 49B often moderately suffused near the edge with between 53C and 53D. At the point where the petal attaches, there is a large zone of between 10B and 11B.

The under surface color of the intermediate and inner petals is between 36A and 37B sometimes lightly suffused near the edge with between 60A and 60B. The upper surface color of the intermediate and inner petals is between 37C and 38B sometimes lightly suffused near the edge with between 53C and 53D.

The under and upper surface colors of the petaloids are similar in coloration to the upper and under surfaces of the intermediate and inner petals.

The general tonality of the newly opened flower is between 37C and 38B.

THREE-DAY-OLD FLOWER

The under-surface color of the outer petals is between 54D and 55D often moderately suffused with near 60D to as dark as between 60B and 60C. At the point where the petal attaches, there is a moderately small zone of between 2D and 1D. The upper surface color of the outer petals is between 36B and 50D often moderately suffused with near 60D to as dark as between 60B and 53C. At the point where the petal attaches, there is a large zone of between 10D and 11C.

The under surface color of the intermediate and inner petals is between 38D and 55D sometimes lightly suffused with near 60D. The upper surface color of the intermediate and inner petals is between 36A and 50D sometimes lightly suffused with near 60D to as dark as between 60B and 53C.

The under and upper surface colors of the petaloids are similar in coloration to the upper and under surfaces of the intermediate and inner petals.

The general tonality of the three-day-old flower is between 36A and 50D.

On the spent bloom, the petals usually drop off cleanly.

In November in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 215) and are arranged regularly about the pistils; a few are mixed with petaloids. The filaments are of somewhat short to medium length (about 0.4 to about 0.9 cm.) most with anthers. Filaments are between 12B and 13C in color sometimes lightly suffused with between 53C and 53D. The anthers are of medium size for the class and all open approximately at the same time. Anther color when immature is near 20A on the external part and near 11D on the internal part. Anther color at maturity is near 163C on the external part and near 200A on the internal part. Pollen is abundant and between 19C and 20C in color.

FEMALE REPRODUCTIVE ORGANS

Pistils vary in number (average about 335). The styles are moderately even, somewhat short to average in length (about 0.3 to about 0.9 cm.), average in caliper, and moderately separated to loosely bunched. Stigma color is between 18B and 19C. Style color is between 4D and 2D usually heavily suffused with between 60A and 60B. Ovaries are usually all enclosed in the calyx. The ovaries are of small size and between 158B and 158C in color.

Hips have not been observed on this variety when grown in Wasco, Calif.

FOLIAGE

The compound leaves are usually comprised of three to seven leaflets and are borne abundantly. The five-leaflet leaves are about 7.5 to about 14.1 cm. in length and about 6.2 to about 10.8 cm. in width at the widest point, leathery to somewhat crisp in texture on both sides, and glossy in finish on the upper side and somewhat semi-glossy to matte in finish on the underside. The leaves have a pinnate venation pattern. The terminal leaflets are about 4.2 to about 7.0 cm. in length and about 2.5 to about 4.4 cm. in width at the widest point, shaped ovate with acute apices and rounded bases. Their margins are usually simply serrate.

The upper surface color of the mature leaf is between 139A and 147A. The under-surface color of the mature leaf is between 147B and 146B. The under and upper colors of the leaf veins on the mature leaf are similar in coloration to the upper and under surfaces colors of the mature leaf. The upper surface color of the young leaf is between 137B and 146A, usually heavily suffused with between 187B and 187A. The under-surface color of the young leaf is between 146C and 138B, usually heavily suffused with between 187B and 187A. The under and upper colors of the leaf veins on the young leaf are similar in coloration to the upper and under surfaces colors of the young leaf.

The rachis is about 2.5 to about 4.8 cm. in length, about 0.1 to about 0.15 cm in width at the widest point, and moderately rough. The upper side is deeply grooved with very few hairs and few stipitate glands on the edges of the grooves. The under side of the rachis is moderately rough with few stipitate glands and very few small prickles. The rachis color is near 146D on the underside and near 137C on the upper side, often moderately suffused on the young leaves with between 187B and 187C.

The stipules are about 1.0 to about 2.0 cm. in length and of somewhat narrow to medium width (about 0.3 to about 0.6 cm.) with moderately short to medium length straight points that usually turn out at an angle of more than 45 degrees and often recurve toward the stem. The under and upper surface color of the stipule is between 137B and 137C often lightly suffused on the young leaves with between 187B and 187C. The upper and under surfaces of the stipules are smooth in texture.

The petiole is moderately light to average in caliper and moderately rough. The upper side is deeply grooved with very few hairs and few stipitate glands on the edges of the grooves. The under side of the petiole is moderately rough with few stipitate glands and very few small prickles. The petiole is about 0.4 to about 1.5 cm. in length and about 0.1 to about 0.15 cm in width at the widest point. The petiole color is near 146D on the underside and near 137C on the upper side, often moderately suffused on the young leaves with between 187B and 187C.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, Calif. The plant's winter hardiness and drought/heat tolerance are yet to be determined.

GROWTH

The plant has an upright tall growing habit (about 155 to about 195 cm. in height and about 52 to about 76 cm. spread at the widest point), with full branching. It displays vigorous growth, and the canes are of somewhat light to medium caliper for the class (about 1.0 to about 2.3 cm. in diameter at the widest point).

The color of the major stems is between 146B and 146A. The major stems are rough in texture, and they bear many large prickles that are about 0.7 to about 1.1 cm. in length. The large prickles are angled slightly downward with a moderately long somewhat narrow oval base; prickle color is between 164A and 165B. The major stem bears some small prickles of similar shape and coloration.

The color of the branches is between 137C and 146B. The branches are rough in texture, and they bear many large prickles which are of similar size and shape to the large prickles on the major stems; prickle color is between 162B and 160A. The branches bear some small prickles of similar shape and coloration.

The color of the new shoots is between 137C and 146B often moderately suffused with between 187B and 187A. The new shoots are rough in texture, and they bear many large prickles which are of similar size and shape to the large prickles on the major stems; prickle color is between 146C and 152C often heavily suffused with between 187B and 187C. The shoots bear some small prickles of similar shape and coloration.

I claim:

1. A new and distinct Hybrid Tea rose plant of the variety designated 'WEKvodomer' substantially as described and illustrated herein.

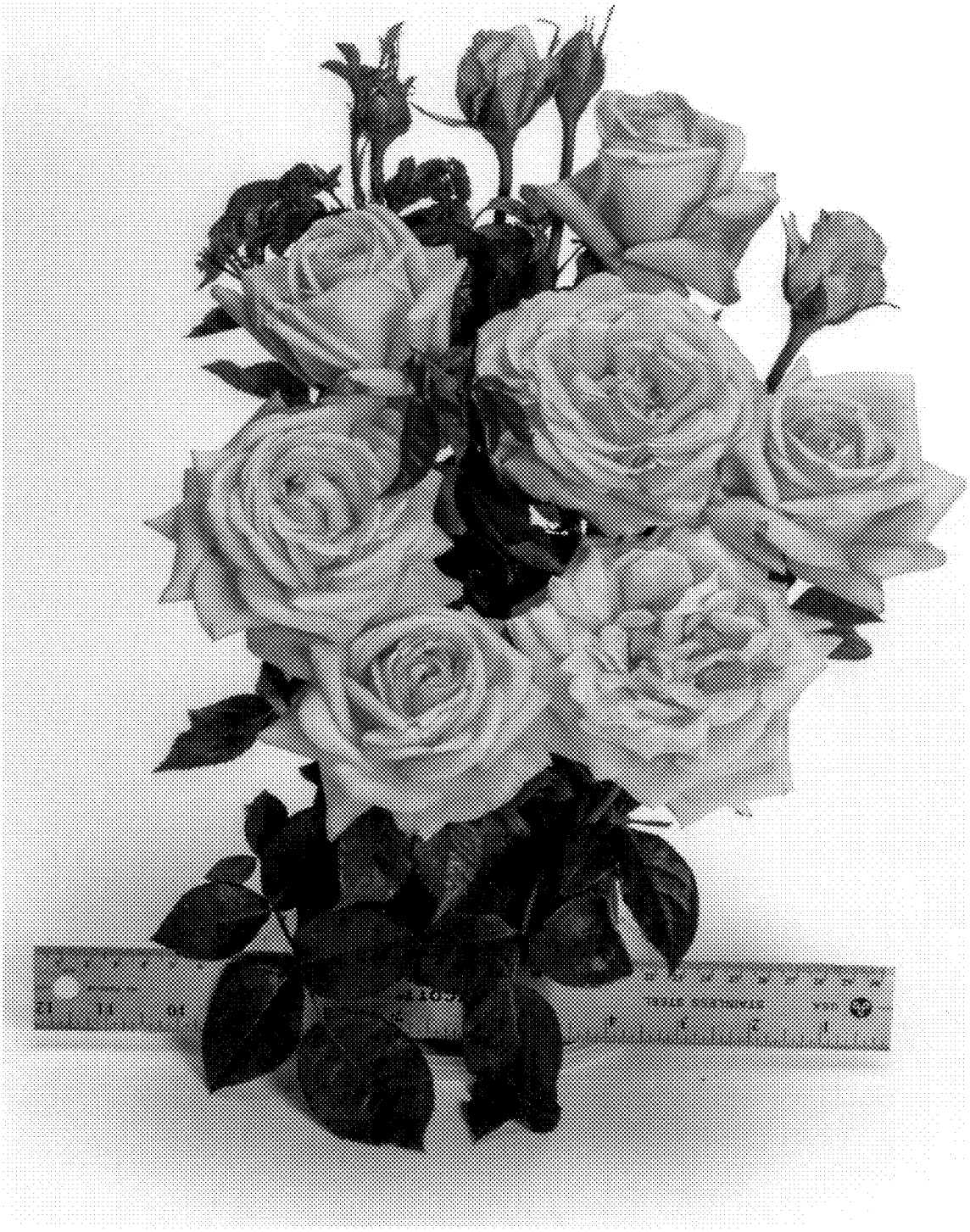

* * * * *